United States Patent [19]

Shin et al.

[11] Patent Number: 5,021,169
[45] Date of Patent: Jun. 4, 1991

[54] ALKENYL SUCCINIC ANHYDRIDES PROCESS

[75] Inventors: Kju H. Shin; Paul S. Hale, both of Baton Rouge, La.

[73] Assignee: Ethyl Corporation, Richmond, Va.

[21] Appl. No.: 435,267

[22] Filed: Nov. 13, 1989

[51] Int. Cl.$^5$ ............................................ C07D 307/60
[52] U.S. Cl. ....................................... 549/255; 549/203
[58] Field of Search ................................. 549/255, 203

[56] References Cited

U.S. PATENT DOCUMENTS 3,476,774 11/1969 Zaweski et al. ..................... 549/255
4,235,786 11/1980 Wisotsky .............................. 549/255

FOREIGN PATENT DOCUMENTS 49-116023 11/1974 Japan.
56-12382 6/1981 Japan.

OTHER PUBLICATIONS

Gaylord et al., J. of Polymer Sci. Part A: Polymer Chemistry, vol. 26, pp. 1903–1909 (Jul. 1988).

Primary Examiner—Bernard I. Dentz
Attorney, Agent, or Firm—David M. Bunnell; Joseph D. Odenweller

[57] ABSTRACT

Alkenyl succinic anhydrides having a decreased amount of tar and color bodies are made by the reaction of an olefin with maleic anhydride in the presence of a tri-orthoalkylphenyl phosphite and optionally a hindered phenolic antioxidant such as 2,4,6-tri-(3,5-di-tert-butyl-4-hydroxybenzyl) mesitylene.

7 Claims, No Drawings

ALKENYL SUCCINIC ANHYDRIDES PROCESS

BACKGROUND

Alkenyl succinic anhydrides ("ASA") are used as sizing agents, bleach activators and as corrosion inhibitors and detergents in petroleum products. They are also readily converted to derivatives such as esters, amides and imides useful in petroleum products.

The thermal process of making ASA requires heating of an olefin and maleic anhydride ("MA") to fairly high temperatures on the order of 175°–275° C. If desired the reaction can be promoted by addition of chlorine. Some degradation occurs in the reaction mixture caused by homopolymerization of MA and copolymerization of MA and olefin leading to discoloration and formation of tar and particulates. These decomposition products have an adverse effect on the color and performance of ASA in many of its leading markets such as paper size.

Attempts have been made to inhibit the formation of tar in the reaction of olefin with MA. Key et al., GB 1,337,724, describe the use of certain phosphorus-containing sequestrants, e.g. triphenylphosphite and hydroxy aromatics to inhibit tar formation in making ASA for use as a detergent builder.

Irwin et al., U.S. Pat. No. 3,412,111, describe the use of hydroxy aromatics, e.g. hydroquinone, and amino aromatics, e.g. phenothiazine, to inhibit polymer formation during preparation of ASA.

Puskas et al., U.S. Pat. No. 3,935,249, disclose the use of small amounts of inorganic halogen compound such as dry HCl or calcium bromide to prevent tar formation.

Zaweski et al., U.S. Pat. No. 3,476,774, report the use of hindered phenols, e.g. 4,4'-methylenebis(2,6-di-tert-butylphenol) and 1,3,5-trimethyl-2,4,6-tri(3,5-di-tert-butyl-4-hydroxybenzyl) benzene, to prevent decomposition of the reactants.

Kao Soap in Japan 56/12382 describe the use of certain phosphite esters, e.g. tributyl phosphite, in making ASA. Japan 60/78975 report the use of a combination of trialkyl phosphite, e.g. trioctyl phosphite, and dihydroxy aromatic, e.g. 2,5-di-tert-butylhydroquinone, in the preparation of ASA.

SUMMARY

It has now been discovered that greater reduction in the amount of discoloration and tar formation can be achieved by preparing ASA in the presence of a tri-ortho-tert-alkylphenyl phosphite.

DESCRIPTION OF THE PREFERRED EMBODIMENTS

A preferred embodiment of the invention is a process for making an alkenyl succinic anhydride having reduced levels of tar and color bodies, said process comprising reacting maleic anhydride with an aliphatic olefin containing about 4–250 carbon atoms at a temperature of about 190°–250° C. in the presence of a stabilizing amount of a triarylphosphite having the structure

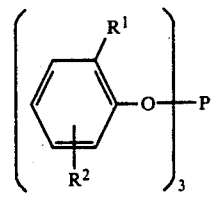

wherein $R^1$ is a tert-alkyl group containing 4–12 carbon atoms and $R^2$ is an alkyl group containing 1–12 carbon atoms.

Examples of useful tri-(ortho-tert-alkylphenyl) phosphites are tri-(2-tert-butylphenyl) phosphite, tri-(2-tert-hexyl-4-methylphenyl) phosphite, tri-(2,5-di-tert-butylphenyl) phosphite, tri-[2-(1,1-dimethyl decyl) phenyl] phosphite, tri-(2-tert-octyl-5-ethylphenyl) phosphite, di-(2-tert-butylphenyl) 2,5-di-tert-butylphenyl phosphite, tri-(2-tert-decyl-5-isopropylphenyl) phosphite, tri-(2,5-di-tert-dodecylphenyl) phosphite and the like including mixtures thereof.

More preferably the tri-(ortho-alkylphenyl) phosphite is a tri-(2-tert-$C_{4-12}$ alkyl-4-$C_{1-12}$ alkylphenyl) phosphite. Some representative examples of these are tri-(2-tert-octyl-4-methylphenyl) phosphite, tri-(2-tert-butyl-4-isopropylphenyl) phosphite, tri-(2-tert-butyl-4-n-dodecylphenyl) phosphite, tri-(2-tert-dodecyl-4-isobutylphenyl) phosphite and the like.

In a still more preferred embodiment the triarylphosphite is a tri-(2,4-di-tert-$C_{4-12}$ alkylphenyl) phosphite. Some examples of this more preferred group of phosphites are tri-(2,4-di-tert-hexylphenyl) phosphite, tri-(2-tert-butyl-4-tert-dodecylphenyl) phosphite, tri-(2,4-di-tert-dodecylphenyl) phosphite, di-(2,4-di-tert-butylphenyl) 2,4-di-tert-octylphenyl phosphite, tri-(2-tert-decyl-4-tert-octylphenyl) phosphite and the like including mixtures thereof.

The most preferred phosphite is tri-(2,4-di-tertbutylphenyl) phosphite.

The alkenyl succinic anhydrides (ASA) are made by heating a mixture of maleic anhydride (MA) and aliphatic olefin at a temperature of about 175°–275° C. The molecular weight of the olefin can vary widely depending upon the intended use of the ASA. paper size ASA have an alkenyl group of about 12–22 carbon atoms. Corrosion inhibitors and fuel detergents generally have an alkenyl group of about 16–35 carbon atoms ASA, used to make imides, amides and esters for use as lubricating oil dispersants, have an alkenyl group of about 40–250 carbon atoms. With the very high molecular weight ASAs, it is more accurate to refer to number average molecular weight $\overline{Mn}$ ) since the olefins used to make these ASAs are a mixture of different molecular weight components resulting from the polymerization of low molecular weight olefin monomers such as ethylene, propylene and isobutylene.

The olefins may be linear or branched. For example, olefins derived from triethyl aluminum/ethylene chain growth via so-called Ziegler chemistry are mainly linear α-olefins. Olefins derived from the polymerization of isobutylene have repeating methyl branching. Both are useful in the present process.

Internal olefins include as those made by isomerizing α-olefins or by dimerizing α-olefins. For example, isomerized $C_{16-18}$ α-olefin or Friedel Craft catalyzed 1-deoene dimer form an ASA having excellent paper sizing properties. Likewise the aluminum alkyl catalyzed dimerization of $C_{8-12}$ α-olefins forms $C_{16-24}$ vinylidene olefins that can be used to make useful ASA paper size.

The reaction is carried out by heating a mixture of MA, an olefin and a small amount of tri-(ortho-tert-alkylphenyl) phosphite to a reaction temperature of about 150°–300° C., more preferably 175°–275° C. and most preferably 200°–250° C. The reaction is preferably conducted in a sealed reaction vessel under autogenous pressure to prevent loss of reactants. Maleic anhydride boils at 202° C.

The mole ratio of MA to olefin can vary widely. It can vary, for example, from 5:1 to 1:5. A more preferred range is 3:1 to 1:3. With the high molecular weight olefins such as polyisobutylene having a number average molecular weight of 900–5000 or higher, the MA is preferably used in stoichiometric excess, e.g. 1.1–5 moles MA per mole of olefin. The unreacted MA can be vaporized from the resultant reaction mixture.

With the lower molecular weight olefins as used in making paper size and corrosion inhibitors, e.g. $\overline{M}n$ of 200–350, either can be used in excess or they can be reacted in a 1:1 mole ratio. Usually an excess of olefin is used, e.g. 1.1–3 moles of olefin per mole MA.

The amount of tri-(ortho-tert-alkylphenyl) phosphite is a small but effective amount. The optimum amount can easily be determined experimentally by gradually increasing the amount of tri-(ortho-tert-alkylphenyl) phosphite until the color and tar formation decreases to the desired level. A useful range in which to conduct these experiments is about 0.05–2.0 weight percent based on the MA charge. A more preferred amount is about 0.1–1.0 weight percent of the MA charge.

The following examples show the process in making an ASA used as a paper size. Example 1 does not use any additive and is for comparative purposes. Example 2 uses a trialkyl phosphite and Example 3 uses triphenyl phosphite in the ASA process and are also for comparative purposes.

EXAMPLE 1 (Comparative)

In an autoclave was placed 60.71 g of mixed $C_{16}/C_{18}$ internal olefins (made by isomerizing the corresponding α-olefins) and 12.46 g of MA. The autoclave was purged with nitrogen, sealed and heated while stirring to 230° C. (~20 minutes heat-up). After 5 hours total reaction time the autoclave was cooled and discharged to obtain a dark orange product containing some black solids (Gardner Color 11.5). The product was distilled under vacuum using a Kugel-Rohr apparatus to remove unreacted olefin, MA and ASA having a polymeric residue equal to 15.7 weight percent of the reaction mixture.

EXAMPLE 2 (Comparative)

In an autoclave was placed 83.51 g of mixed, $C_{16}/C_{18}$ internal olefins, 17.16 g MA and 0.1287 g tributyl phosphite. The autoclave was flushed with nitrogen, sealed and stirred while heating to 230° C. After a 5-hour total reaction period the autoclave was cooled and discharged. The product was orange and contained many black specks. The interior of the autoclave was heavily varnished. The crude product has a Gardner color of 10.5.

EXAMPLE 3 (Comparative)

In an autoclave was placed 81.62 g mixed $C_{16}/C_{18}$ internal olefins (same source as Example 1), 16.7 g MA and 0.126 g of triphenyl phosphite. The autoclave was flushed with nitrogen, sealed and while stirring heated to 230° C. as in Example 1. The autoclave was then cooled and discharged to give a light yellow product (Gardner Color 6.0). The product was distilled as in Example 1 to give 12.0 weight percent residual polymer.

The following examples show the results obtained when making an ASA according to the present process.

EXAMPLE 4

In an autoclave was placed 81.55 mixed internal $C_{16}/C_{18}$ olefins prepared by isomerizing $C_{16}/C_{18}$ α-olefins. To this was added 16.77 g MA and 0.126 g tri-(2,4-di-tert-butylphenyl) phosphite. The autoclave was purged with nitrogen, sealed and, while stirring, heated to 230° C. over 16 minutes. Stirring at 230° C. was continued to a 5 hour total lapsed time. The autoclave was cooled and discharged. Inspection of the autoclave showed very little varnish formation. The crude product had a Gardner Color of 5.5. The product was distilled as in Example 1 resulting in 8.0 g of residual polymer.

The following table compares the color of the ASA products made in the examples.

| Example | Additive | Polymeric Residue (wt %) | Gardner Color |
|---|---|---|---|
| 1 | none | 15.7 | 11.5 |
| 2 | tributyl phosphite | 6.9 | 10.5 |
| 3 | triphenyl phosphite | 12.7 | 6.0 |
| 4 | tri-(2,4-di-tert-butyl phenyl)phosphite | 8.0 | 5.5 |

These results show that the tri-(ortho-alkylphenyl)-phosphite of this invention results in both low color and low residual polymer.

When used as paper size, the unreacted olefin and MA are distilled out and the entire remaining product is used as paper size. This is why it is important to have a light colored product with polymeric products as low as possible.

The tri-(ortho-tert-alkylphenyl) phosphite can be used alone in the process or they can be used in combination with hindered phenolic antioxidants including all those disclosed in Zaweski et al., U.S. Pat. No. 3,476,774, (incorporated herein by reference). These include 4,4'-methylene(2,6-di-tert-butylphenyl), pentaerythritol tetrakis [3-(3,5-di-tert-butyl-4-hydroxyphenyl)propionate], 2,4,6-tri(3,5-di-tert-butyl-4-hydroxybenzyl) mesitylene, and the like.

We claim:

1. A process for making an alkenyl succinic anhydride having reduced levels of tar and color bodies, said process comprising reacting maleic anhydride with an aliphatic olefin containing about 4–250 carbon atoms at a temperature of about 190°–250° C. in the presence of a triarylphosphite having the structure:

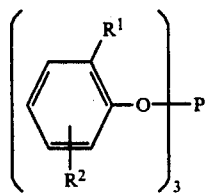

wherein $R^1$ is a tert-alkyl group containing 4–12 carbon atoms and $R^2$ is an alkyl group containing 1–12 carbon atoms.

2. A process of claim 1 wherein said triarylphosphite is a tri-(2-tert-$C_{4-12}$ alkyl-4-$C_{1-12}$ alkylphenyl) phosphite.

3. A process of claim 2 wherein said triarylphosphite is a tri-(2,4-di-tert-$C_{4-12}$ alkylphenyl) phosphite.

4. A process of claim 3 wherein said triarylphosphite is tri-(2,4-di-tert-butylphenyl) phosphite.

5. A process of claim 4 wherein said olefin is a branched or straight chain, terminal or internal olefin containing about 12–24 carbon atoms.

6. A process of claim 5 wherein said olefin is a mixture of mainly internal olefins.

7. A process of claim 6 wherein said mixture of mainly internal olefins is an isomerized α-olefin.

* * * * *